United States Patent [19]

Brown et al.

[11] 4,377,471

[45] Mar. 22, 1983

[54] METHOD FOR REMOVING POLYCHLORINATED BIPHENYLS FROM TRANSFORMER OIL

[75] Inventors: John F. Brown; Marie E. Lynch, both of Schenectady, N.Y.

[73] Assignee: General Electric Company, Schenectady, N.Y.

[21] Appl. No.: 212,387

[22] Filed: Dec. 3, 1980

[51] Int. Cl.$^3$ .................... C10G 45/02; C10G 19/00; C10G 19/073; C07C 1/26

[52] U.S. Cl. .................... 208/262; 585/469; 570/204

[58] Field of Search .................... 208/262; 585/469; 570/204

[56] References Cited

U.S. PATENT DOCUMENTS

| | | | |
|---|---|---|---|
| 564,683 | 10/1958 | Miller et al. | 308/262 |
| 4,284,516 | 8/1981 | Parker et al. | 585/469 |

OTHER PUBLICATIONS

PCB, The Franklin Institute News, vol. 44, No. 2, Jun.-/Jul. 1980.

Disclosure Letter—Destruction of Polychlorinated Biphenyls (PCB) In Mineral Oil, W. A. Fessler—Exhibit A.

Disclosure Letter—W. A. Fessler—Exhibit C.

Disclosure Letter—Treatment for PCB-Contaminated Transformer Oil, John F. Brown et al.—Exhibit B.

A complete Dechlorination of Polychlorinated Biphenyl by Sodium Naphthalene, Oku et al., Chemistry and Industry, 841, 1978.

Conversion of PCBs and Halogenated Pesticides into Non-Toxic Materials Using a New Type of Alkali Metal Reaction, Pytlewski et al., EPA Conference, Chicago, 3/18/80.

The Dechlorination of Polychlorinated Biphenyls by Alkaline Metals and Naphthalene, Oku et al., p. 1582, No. 11, 1978.

Chemical Abstracts, Sewage, Wastes, vol. 82, 1975, Treatment of Poly(chlorinated biphenyl) Wastes, Takase et al., 1974.

Goodyear Develops PCB Removal Method, C & EN, Sep. 1, 1980.

Preprint—University of Waterloo, Nov. 20, 1979—The Chemical Destruction of Polychlorinated Biphenyls by Sodium Naphthalenide, Smith et al.

Preprint—The Goodyear Tire & Rubber Company, A Safe, Efficient Chemical Disposal Method for Polychlorinated Biphenyls—"PCB's" Dane K. Parker.

*Primary Examiner*—Delbert E. Gantz

*Assistant Examiner*—Helane E. Maull

*Attorney, Agent, or Firm*—William A. Teoli; James C. Davis, Jr.

[57] ABSTRACT

A method is provided for effecting the removal of polychlorinated biphenyls from hydrocarbon oils, such as transformer oil, contaminated with more than 50 ppm of such polychlorinated biphenyls. There is utilized in the contaminated oil, while it is being agitated, dispersed metallic sodium, an aprotic ion-complexing solvent, for example, diglyme, and an oil-soluble electron carrier, such as naphthalene.

6 Claims, No Drawings

METHOD FOR REMOVING POLYCHLORINATED BIPHENYLS FROM TRANSFORMER OIL

BACKGROUND OF THE INVENTION

Polychlorinated biphenyls, or "PCB's" were, long used as dielectric fluids in electrical equipment because these materials have excellent heat stability, are nonflammable in nature, have low volatility and a good viscosity characteristic at operating temperatures. Because of their environmental persistence, however, continued manufacture, import, or use in the United States was banned under the Toxic Substances Control Act of 1976, and the U.S. Environmental Protection Agency was directed to promulgate rules and regulations for their removal from the economy.

As of July 1, 1979, EPA regulations define as "PCB-contaminated" any material containing more than 50 ppm of a mono-, di-, or polychlorinated biphenyl. The regulations permit disposal of PCB-contaminated materials by either incineration in an approved manner or in an approved landfill, but such procedures have rarely proven acceptable to community neighbors. Since considerable fractions of the transformer oils, e.g., refined asphaltic-base mineral oil, or heat exchange oils, e.g., hydrogenated terphenyls, now in serivce are PCB-contaminated, the problem of disposing of PCB-contaminated hydrocarbon oils in an effective manner presents a serious challenge. As used hereinafter, the term "transformer oil" signifies a mineral insulating oil of petroleum origin for use as an insulating and cooling media in electrical apparatus, for example, transformers, capacitors, underground cables, etc.

Various techniques for meeting this challenge have been proposed. One method is shown by D. K. Parker et al, Plant Engineering, Aug. 21, 1980, Pages 133–134. The method of Parker et al is based on the formation of a solution of an organo-sodium reagent, such as sodium naphthalenide, in a carrier solvent, for example, tetrahydrofuran, which is then added to the contaminated oil. The Parker et al process requires a multistep procedure involving first the formation of organo-sodium reagent, next the incorporation of such organo-sodium compound into the PCB-contaminated oil followed by at least 2 more hours for the reaction to be complete, followed by a water quench and distillation and purification steps to recycle the tetrahydrofuran. Another procedure, somewhat similar to the Parker et al process, is described by Smith et al, University of Waterloo, based on the graduate thesis of James G. Smith and G. L. Bubbar, "The Chemical Destruction of Polychlorinated Biphenyls by Sodium Napthalenide". Again, a lengthy, multistep procedure is necessary before effective destruction of the PCB is achieved. A further procedure is shown by Hiraoka et al, Japan Kokai 74 822,570, Chem. Abstracts 89831K, Vol. 82, 1975, which describes the destruction of polychlorinated biphenyls utilizing a sodium dispersion in kerosene, but requires a 6 hour heating period at 120° C.

The present invention is based on the discovery that destruction of PCB's can be achieved directly without the necessity of preforming an organo-sodium reagent, by adding finely divided sodium metal directly into PCB-contaminated transformer oil along with a suitable organic electron carrier, such as benzophenone, biphenyl, naphthalene, etc., and an aprotic ion-solvating solvent, such as diglyme, or tetrahydrofuran, etc., while agitating the mixture under an inert atmosphere. The direct addition of finely divided sodium metal to the PCB-contaminated mixture eliminates the several hours of processing required in making the preformed sodium complex. Further, the direct addition of the organic electron carrier and aprotic ion-solvating solvent along with the sodium metal has been found to significantly reduce total reaction time, limit the requirements for ion-complexing solvent to the point where the solvent recovery and recycling steps are unnecessary, and to permit the reaction to be carried out at ambient temperatures.

STATEMENT OF THE INVENTION

There is provided by the present invention, a method which comprises, agitating under an inert atmosphere, a mixture comprising by weight (A) contaminated transformer oil having up to 1% by weight of polychlorinated biphenyl and less than 60 ppm of water, (B) 0.1 to 2% of finely divided sodium metal, (C) 1 to 10% of an aprotic ion-complexing solvent, and (D) 0.1 to 1% of an oil-soluble electron carrier, where agitation of the mixture is continued until the polychlorinated biphenyl content of the mixture is reduced to less than 50 ppm, and the weight of (B), (C) and (D), respectively is based on the weight of (A).

There is included within the definition of aprotic ion-complexing solvent, materials such as tetrahydrofuran, ethylene glycol dimethyl ether ("glyme"), diethylene glycol dimethyl ether ("diglyme"), other oligomeric ethylene glycol dialkyl ethers ("triglyme", "tetraglyme", etc.), dimethyl formamide, hexamethyl phosphoramide, etc.

Among the oil-soluble electron carriers which can be utilized in the practice of the present invention, there are included, for example, benzophenone, alkylated benzophenones, naphthalene, alkyl naphthalenes, biphenyl, alkyl biphenyls, etc.

In the practice of the present invention, a dispersion of finely divided sodium metal is incorporated into the PCB-contaminated oil while it is agitated under an inert atmosphere at ambient temperatures. Preferably, the oil-soluble electron carrier is then added as a solution in the aprotic ion-complexing solvent. However, it has been found that the order of addition of the aforementioned ingredients is not critical. Finely divided sodium metal can be obtained by heating fresh sodium metal in an inert mineral oil having low volatility at 150°–170° C. for 5–10 minutes with vigorous stirring under an inert atmosphere, such as nitrogen, or purchased from commercial sources (e.g., Coronet Chemical Company, Newark, N.J.).

In order to avoid possible reaction of the sodium metal with the water which might be present in the contaminated transformer oil, the transformer oil should be carefully dried within the above-described limits prior to the addition of metallic sodium. One method, for example, is to pass the oil through a molecular sieve. Preferably, total water content should not exceed 60 ppm of the oil. At the termination of the reaction, the mixture can be filtered to effect the removal of salts if desired to make the decontaminated oil commercially reusable.

The level of PCB-contamination before and after treatment can be readily determined by use of gas chromatography in accordance with the procedure of O. Hutzinger et al, the Chemistry of PCB, Chemical Rubber Company Press Inc., 1974, pp. 197–218.

In order that those skilled in the art will be better able to practice the invention, the following examples are given by way of illustration and not by way of limitation. All parts are by weight.

EXAMPLE 1

There was added 0.2 part of sodium metal in the form of a 40% dispersion in a light mineral oil (Matheson, Coleman and Bell), along with 0.23% by weight of benzophenone and 3% by weight of diethylene glycol dimethylether as a solution to 100 parts of transformer oil having about 800 ppm of Aroclor 1260 and less than 60 ppm of water. The additions were carried out under a nitrogen atmosphere at about 24° C. The mixture was stirred for 3 hours and analysis by gas chromatography showed that the PCB level was reduced to about 0.7 ppm.

EXAMPLE 2

There was added 0.28 parts of sodium metal as a 20% dispersion in mineral oil (Coronet Chemical) and a solution of 0.35 parts of naphthalene in 5 parts of diethylene glycol dimethylether to 100 parts of transformer oil contaminated with 832 ppm of Aroclor 1260. The contaminated oil had been passed through a column of Linde 4A Molecular Sieve No. 87956 to effect the removal of excess water. The mixture was stirred at ambient temperatures and gas chromatographic analysis showed the presence of only about 17 ppm of PCB after 15 minutes stirring and 1 ppm after 1 hour.

EXAMPLE 3

There are added at ambient temperatures under a nitrogen atmosphere, 0.15 part of finely divided sodium metal in mineral oil, and 0.35 part of naphthalene in 15 parts of diethylene glycol dimethyl ether to 100 parts of transformer oil contaminated with 100 ppm of Aroclor 1260. The contaminated oil has less than 60 ppm of water. After the mixture is stirred for two hours, gas chromatographic analysis shows the mixture contains less than 1 ppm of PCB.

Although the above examples are directed to only a few of the very many variables in the method of the present invention, it should be understood that the present invention is directed to the use of a much broader variety of aprotic ion-complexing solvents and oil-soluble electron carriers which are shown in the description preceding these examples.

What we claim as new and desire to secure by Letters Patent of the United States is:

1. A method for effecting the removal of polychlorinated biphenyls from contaminated transformer oil having up to 1% by weight of polychlorinated biphenyl, and less 60 ppm of water which comprises (1) directly adding to the transformer oil under an inert atmosphere, while it is being agitated, finely divided sodium metal, an oil soluble electron carrier selected from the class consisting of benzophenone, alkylated benzophenone, naphthylene, alkyl naphthylene, biphenyl and alkyl biphenyl, and an aprotic complexing solvent selected from the class consisting of tetrahydrofuran, ethyleneglycoldimethylether, diethyleneglycoldimethylether, oligomeric ethyleneglycoldialkylether, dimethylformamide and hexamethylphosphoramide, and (2) continuing the agitation of the resulting mixture until the polychlorinated biphenyl content of the resulting mixture is reduced to less than 50 ppm, where the aforementioned ingredients of (1) are utilized in proportions sufficient to produce a mixture having an initial concentration of 0.1–2% of the finely divided sodium metal, 0.1 to 1% of oil soluble electron, and 1–10% of the aprotic complexing solvent, based on the weight of the mixture.

2. A method in accordance with claim 1, where the aprotic ion-complexing solvent is diethylene glycol dimethylether.

3. A method in accordance with claim 1, where the oil-soluble electron carrier is benzophenone.

4. A method in accordance with claim 1, where the oil-soluble electron carrier is naphthalene.

5. A method in accordance with claim 1, where the aprotic ion-complexing solvent is tetrahydrofuran.

6. A method in accordance with claim 1, where the oil-soluble electron carrier is biphenyl.

* * * * *